(12) United States Patent
Linnes et al.

(10) Patent No.: US 10,786,201 B2
(45) Date of Patent: Sep. 29, 2020

(54) METHODS FOR DETECTING HEART RATE, RESPIRATION, AND OXYGEN SATURATION AND USES THEREOF

(71) Applicant: Purdue Research Foundation, West Lafayette, IN (US)

(72) Inventors: Jacqueline Callihan Linnes, West Lafayette, IN (US); Orlando Sanguinette Hoilett, West Lafayette, IN (US); Ashlyn Twibell, South Bend, IN (US); Hyowon Lee, West Lafayette, IN (US); Rohit Srivastava, Ballwin, MT (US); Jason D Ummel, Greencastle, IN (US); Ryan Lindsey, Evansville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/159,007

(22) Filed: Oct. 12, 2018

(65) Prior Publication Data

US 2019/0110745 A1 Apr. 18, 2019

Related U.S. Application Data

(60) Provisional application No. 62/571,299, filed on Oct. 12, 2017.

(51) Int. Cl.
*A61B 5/00* (2006.01)
*A61B 5/0205* (2006.01)
(Continued)

(52) U.S. Cl.
CPC ............ *A61B 5/681* (2013.01); *A61B 5/0205* (2013.01); *A61B 5/1112* (2013.01); *A61B 5/14552* (2013.01); *A61B 5/4833* (2013.01); *A61B 5/7207* (2013.01); *A61B 5/7257* (2013.01); *A61B 5/743* (2013.01); *A61B 5/0022* (2013.01); *A61B 5/02433* (2013.01);
(Continued)

(58) Field of Classification Search
CPC ... A61B 5/681; A61B 5/14552; A61B 5/4833; A61B 5/1112; A61B 5/743; A61B 5/7257; A61B 5/7207; A61B 5/0205; A61B 5/0816; A61B 5/02433; A61B 5/0022; A61B 2562/0219; A61B 2560/0228; A61B 2560/0214; A61B 2503/12
See application file for complete search history.

(56) References Cited

U.S. PATENT DOCUMENTS

2014/0275854 A1* 9/2014 Venkatraman ......... A61B 5/721
600/301

OTHER PUBLICATIONS

Allen, J., "Photoplethysmography and its application in clinical physiological measurement," Physiol. Meas., vol. 28, No. 3, 2007, pp. R1-R39.

(Continued)

*Primary Examiner* — Mallika D Fairchild
(74) *Attorney, Agent, or Firm* — Piroozi-IP, LLC

(57) ABSTRACT

This invention generally relates to methods useful for measuring heart rate, respiration conditions, and oxygen saturation and a wearable device that incorporate those methods with a computerized system supporting data collection, analysis, readout and sharing. Particularly this present invention relates to a wearable device, such as a wrist watch or ring, for real time measuring heart rate, respiration conditions, and oxygen saturation.

10 Claims, 16 Drawing Sheets

(51) Int. Cl.
*A61B 5/11* (2006.01)
*A61B 5/1455* (2006.01)
*A61B 5/024* (2006.01)
*A61B 5/08* (2006.01)

(52) U.S. Cl.
CPC ......... *A61B 5/0816* (2013.01); *A61B 2503/12* (2013.01); *A61B 2560/0214* (2013.01); *A61B 2560/0228* (2013.01); *A61B 2562/0219* (2013.01)

(56) References Cited

OTHER PUBLICATIONS

Spierer, D., et al, "Validation of photoplethysmography as a method to detect heart rate during rest and exercise," J. Med. Eng. Technol., vol. 39, No. 5, Jul. 2015, pp. 264-271.

Fieselmann, J., "Respiratory rate predicts cardiopulmonary arrest for internal medicine inpatients," J. Gen. Intern. Med., vol. 8, No. 7, Jul. 1993, pp. 354-360.

Leonard, P., "Standard pulse oximeters can be used to monitor respiratory rate," Emerg. Med. J. EMJ, vol. 20, No. 6, Nov. 2003, pp. 524-525.

Clifton, D., "Measurement of Respiratory Rate From the Photoplethysmogram in Chest Clinic Patients," J. Clin. Monit. Comput, vol. 21, No. 1, Feb. 2007, pp. 55-61.

Eckberg, D., "Phase relationship between normal human respiration and baroreflex responsiveness.," J. Physiol., vol. 304, No. 1, Jul. 1980, pp. 489-502.

Kim, J., "Battery-free, stretchable optoelectronic systems for wireless optical characterization of the skin," Sci. Adv., vol. 2, No. 8, Aug. 2016, pp. 10.

Kim, J., "Measurement Accuracy of Heart Rate and Respiratory Rate during Graded Exercise and Sustained Exercise in the Heat Using the Zephyr BioHarnessTM," Int. J. Sports Med., vol. 34, No. 6, Jun. 2013, pp. 497-501.

Allen, J., "Short term spectral analysis, synthesis, and modification by discrete Fourier transform," IEEE Trans. Acoust. Speech Signal Process., vol. 25, No. 3, Jun. 1977, pp. 235-238.

* cited by examiner

METHODS FOR DETECTING HEART RATE, RESPIRATION, AND OXYGEN SATURATION AND USES THEREOF

CROSS-REFERENCE TO RELATED APPLICATIONS

The present U.S. patent application relates to and claims the priority benefit of U.S. Provisional Patent Application Ser. No. 62/571,299, filed Oct. 12, 2017, the content of which is hereby incorporated by reference in its entirety.

GOVERNMENT SUPPORT CLAUSE

This invention was made with government support under grant DA038886, awarded by the National Institutes of Health. The government has certain rights in the invention.

STATEMENT OF COMPUTER LISTING

A computer program in a computer-readable form (CRF) is submitted concurrently with this application. The file, entitled 68015-02_computer_listing.txt, is generated on Sep. 5, 2018. The content of the computer listing is hereby incorporated by reference in its entirety.

TECHNICAL FIELD

This invention generally relates to a method useful for measuring heart rate, respiration conditions, and oxygen saturation and a wearable device that incorporate said method with a computerized system supporting data collection, analysis, readout and sharing.

BACKGROUNDS AND SUMMARY OF THE INVENTION

This section introduces aspects that may help facilitate a better understanding of the disclosure. Accordingly, these statements are to be read in this light and are not to be understood as admissions about what is or is not prior art.

Wearable devices are getting more popularity almost on daily basis, rapidly advancing in terms of technology, functionality, and size, with more real-time applications. A wearable device, wearable technology, or a wearable gadget is a category of technology devices that can be worn by a consumer and often include tracking information related to health and fitness. A wearable device as disclosed herein refers to a wrist watch, a ring or a necklace. Any additional capabilities to those device will add more value and enhance their popularity, not only to everyday people on the street, but also to those sick and feeble in need of special cares. Additionally, a wearable device may also find uses in remote monitoring and diagnosis of patients' health conditions.

Photoplethysmography (PPG) is a simple, optical technique used to detect volumetric changes in blood in peripheral circulation. It is a low-cost and non-invasive method that makes measurements at the surface of the skin. PPG makes uses of low intensity infrared (IR) light. When light travels through biological tissues, it is absorbed by bones, skin pigments as well as venous and arterial blood. Since light is more strongly absorbed by blood than other surrounding tissues, the volumetric changes in blood flow can be detected by PPG sensors as changes in the intensity of light. The voltage signal from PPG is proportional to the quantity of blood flowing through the blood vessels. Blood flow variations mostly occur in the arteries, and not much in the veins. Other factors affecting the recordings from the PPG are the site of measurement, the contact force between the site and the sensor, as well as the skin color at the site of measurement.

The measurements provide valuable information related to the cardiovascular system and are widely used in clinical physiological measurements and monitoring, including heart rate and pulse oximetry. Existing PPG technologies apply sensors to the finger, but this technique suffer from lack of mobility. Numerous technologies can be worn on the wrist; however, they are unable to detect respiration or blood oxygenation levels. There is need of more practical method for monitoring health via PPG that can detect all needed measurements.

This invention generally relates to a method useful for measuring heart rate, respiration conditions, and oxygen saturation and a wearable device that incorporate those methods with a computerized system supporting data collection, analysis, readout and sharing. Particularly this present invention relates to a wearable device, such as a wrist watch, for real time measuring heart rate, respiration conditions, and oxygen saturation, wherein those data can be shared and distributed remotely.

BRIEF DESCRIPTION OF THE DRAWINGS

Embodiments of the present disclosure will now be described by way of example in greater detail with reference to the attached figures, in which.

DETAILED DESCRIPTION

Figure 1:
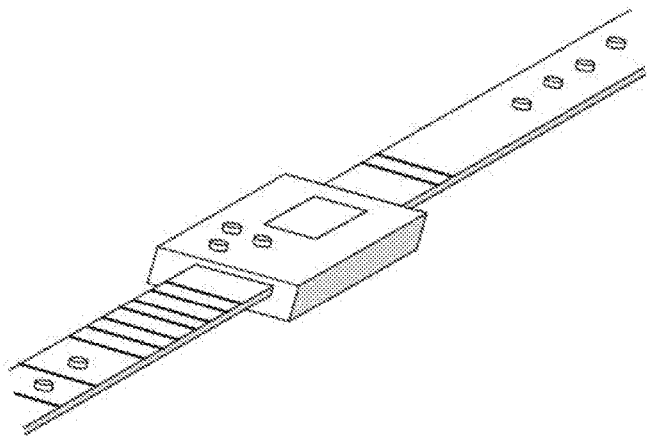
FIG. 1 shows a prototype of a wearable device disclosed herein.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

This invention generally relates to a method useful for measuring heart rate, respiration conditions, and oxygen saturation and a wearable device that incorporate those methods with a computerized system supporting data collection, analysis, and readout. Particularly this present invention relates to a wearable device, such as a wrist watch, a ring or a necklace, for real time measuring heart rate, respiration conditions, and oxygen saturation.

In some illustrative embodiments, the invention relates to a method for measuring heart rate, respiration, and oxygen saturation of a subject comprising extracting and processing photoplethysmographic (PPG) data from said subject and displaying a readout on a wearable device.

In some illustrative embodiments, the invention relates to a method for measuring heart rate, respiration, and oxygen saturation of a subject with a single device comprising the step of
 a) measuring reflectance of red and infrared lights off skin tissue using a biometric sensor board;
 b) processing and analyzing data collected in step a); and
 c) displaying and/or sharing results of the processed data remotely.

In some illustrative embodiments, the invention relates to a method for measuring heart rate, respiration, and oxygen saturation of a subject with a single device as disclosed herein, wherein the subject is a human patient or a healthy subject in need of monitoring for safety purpose.

In some illustrative embodiments, the invention relates to a method for measuring heart rate, respiration, and oxygen saturation of a subject with a single device as disclosed herein, wherein said device is a wearable device comprising a watch, a ring or a necklace.

In some illustrative embodiments, the invention relates to a method for measuring heart rate, respiration, and oxygen saturation of a subject with a single device as disclosed herein, wherein said biometric sensor board extracts and collects photoplethysmographic data from said subject.

In some illustrative embodiments, the invention relates to a method for measuring heart rate, respiration, and oxygen saturation of a subject with a single device as disclosed herein, wherein said biometric sensor board comprises a light sensor, a dual wavelength light source (red and infrared) with an auto-gain feedback loop for calibrating skin tones and pulse strength, and a plurality of active filters for an enhanced signal to noise ratio with an auto-gain feedback loop to maintain a reasonable signal strength for ease of signal processing.

In some illustrative embodiments, the invention relates to a method for measuring heart rate, respiration, and oxygen saturation of a subject with a single device as disclosed herein, wherein said data processing and analyzing carried out by a microcontroller equipped with a central processing unit comprises noises elimination from extracted photoplethysmographic data using a motion tracking sensor for an enhanced signal to noise ratio.

In some illustrative embodiments, the invention relates to a method for measuring heart rate, respiration, and oxygen saturation of a subject with a single device as disclosed herein, wherein said motion tracking sensor is an accelerometer, a gyroscope, or a combination thereof.

In some illustrative embodiments, the invention relates to a method for measuring heart rate, respiration, and oxygen saturation of a subject with a single device as disclosed herein, wherein said data processing and analyzing comprises a frequency analysis using a Fourier Transform on data collected over several seconds of time, wherein said frequency is reasonably related to a biometric measurement of heart rate and respiration.

In some illustrative embodiments, the invention relates to a method for measuring heart rate, respiration, and oxygen saturation of a subject with a single device as disclosed herein, wherein said reasonable frequency for heart rate measurement ranges from about 0.4 Hertz (Hz) to about 4 Hz; said reasonable frequency for respiration measurement ranges from about 0.05 Hz to about 1.2 Hz; and said heart rate and respiration are determined by comparing the magnitude of a peak of the Fourier Transform for heart rate or respiration at each frequency to the magnitude of a peak in the Fourier Transform of the accelerometer/gyroscope data in all three axes at each frequency, respectively.

In some illustrative embodiments, the invention relates to a method for measuring heart rate, respiration, and oxygen saturation of a subject with a single device as disclosed herein, wherein said oxygen saturation in blood of said subject is determined by comparing the relative signal strength of red and infrared light collected over several seconds of time.

In some illustrative embodiments, the invention relates to a wearable device measuring heart rate, respiration and oxygen saturation of a subject can be displayed and/or shared remotely.

In some illustrative embodiments, the invention relates to a wearable device measuring heart rate, respiration and oxygen saturation of a subject can be displayed and/or shared remotely as disclosed herein, which further comprising a means for pinpointing the exact location of said subject for monitoring and detecting drug use or abuse of said subject remotely.

In some illustrative embodiments, the invention relates to a wearable device for measuring heart rate, respiration, and oxygen saturation of a subject comprising a) a biometric sensor board measuring reflectance of red and infrared lights off skin tissue;
b) a microcontroller processing data collected by said photosensor, wherein a dedicated memory chip is installed for storing large amounts of data for real-time signal processing;
c) a power supply; and
d) a means for displaying and/or sharing results of the processed data.

In some illustrative embodiments, the invention relates to a wearable device for measuring heart rate, respiration, and oxygen saturation of a subject in a single device further comprising a motion tracking sensor for an enhanced signal to noise ratio by eliminating noises from extracted photoplethysmographic data.

In some illustrative embodiments, the invention relates to a wearable device for measuring heart rate, respiration, and oxygen saturation of a subject in a single device further comprising a motion tracking sensor for an enhanced signal to noise ratio by eliminating noises from extracted photoplethysmographic data, wherein said motion tracking sensor is an accelerometer, a gyroscope or a combination thereof.

In some illustrative embodiments, the invention relates to a wearable device for measuring heart rate, respiration, and oxygen saturation of a subject in a single device further comprising a real-time clock for accurate time keeping and a means for battery level monitoring.

In some illustrative embodiments, the invention relates to a wearable device for measuring heart rate, respiration, and oxygen saturation of a subject in a single device further comprising a means for pinpointing the location of said subject for monitoring and detecting drug use or abuse of said subject.

In some illustrative embodiments, the invention relates to a wearable device for measuring heart rate, respiration, and oxygen saturation of a subject in a single device further comprising input and output capabilities for charging, programming, and data transfer and sharing.

In some illustrative embodiments, the invention relates to a wearable device for measuring heart rate, respiration, and oxygen saturation of a subject in a single device further comprising means for long term and short term data storage.

In some illustrative embodiments, the invention relates to a wearable device for measuring heart rate, respiration, and oxygen saturation of a subject in a single device, wherein said biometric sensor board comprises a light sensor, a dual wavelength light source (red and infrared) with an auto-gain feedback loop for calibrating skin tones and pulse strength, and a plurality of active filters for an enhanced signal to noise ratio with an auto-gain feedback loop to maintain a reasonable signal strength for ease of signal processing.

In some illustrative embodiments, the invention relates to a wearable device for measuring heart rate, respiration, and oxygen saturation of a subject in a single device, wherein said heart rate, respiration, and oxygen saturation of a subject are measured, displayed and shared in a single device.

In some illustrative embodiments, the invention relates to a wearable device for measuring heart rate, respiration, and oxygen saturation of a subject in a single device, wherein said heart rate, respiration, and oxygen saturation of a subject are shared and/or monitored remotely.

In some illustrative embodiments, the invention relates to a wearable device for measuring heart rate, respiration, and oxygen saturation of a subject in a single device, wherein said data processing and analyzing comprises a frequency analysis using a Fourier Transform on data collected over several seconds of time, wherein said frequency is reasonably related to a specific biometric measurement of heart rate and respiration.

In some illustrative embodiments, the invention relates to a wearable device for measuring heart rate, respiration, and oxygen saturation of a subject in a single device, wherein said data processing and analyzing comprises a frequency analysis using a Fourier Transform on data collected over several seconds of time, wherein said frequency is reasonably related to a specific biometric measurement of heart rate and respiration, and wherein said reasonable frequency for heart rate measurement ranges from about 0.4 Hertz (Hz) to about 4 Hz; said reasonable frequency for respiration measurement ranges from about 0.05 Hz to about 1.2 Hz; and said heart rate and respiration are determined by comparing the magnitude of a peak of the Fourier Transform for heart rate and respiration at each frequency to the magnitude of a peak in the Fourier Transform of the accelerometer/gyroscope data in all three axes at each frequency, respectively.

In some illustrative embodiments, the invention relates to a wearable device for measuring heart rate, respiration, and oxygen saturation of a subject in a single device, wherein said data processing and analyzing comprises a frequency analysis using a Fourier Transform on data collected over several seconds of time, and wherein said oxygen saturation in blood of said subject is determined by comparing relative signal strength of red and infrared light collected over several seconds of time.

Methods to measure physiological signals, such as heart rate, using photoplethysmography (PPG) detect changes in the volume of blood flowing through blood vessels due to the rhythmic activity of the heart (J. Allen, *Physiol. Meas.* 2007, 28(3), p. R1). This volume change is measured by illuminating the capillary bed with a small light source and measuring the amount of light that reflects or passes through the tissue with a photodiode. This technique has been utilized at length in consumer fitness devices for continuous monitoring of heart rate during rest and exercise (DK Spierer, et al., *J. Med. Eng. Technol.*, 2015, 39(5), 264-271). Though heart rate monitoring is undoubtedly beneficial for monitoring general health and activity levels, more sensing capabilities are needed to provide a more holistic picture of human health. Of these additional sensing capabilities, respiration is of particular value since it provides a more comprehensive evaluation of cardiopulmonary activity when coupled with heart rate monitoring (J F Fieselmann, et al., *J. Gen. Intern. Med.*, 1993, 8(7), 354-360). Respiratory monitoring provides additional clinical diagnostic capabilities for diagnosing anomalies such as sleep apnea, hyperventilation, and panic disorders. As such, respiratory rate measurements have extensive clinical utility. Conveniently, PPG has also been shown to measure respiratory signals in addition to heart rate (P Leonard, et al., *Emerg. Med. J. EMJ*, 2003, 20(6), 524-525; D Clifton, et al., *J. Clin. Monit. Comput.*, 2007, 21(1), 55-61). This suggests that there is a possibility of monitoring respiratory and heart rate with a single device by analyzing the PPG signal.

In addition to sensing capabilities and detection modalities, the choice of form factor is critical. For heart rate measurements, both chest strap and wrist-worn devices have been developed. However, chest straps are known for their level of discomfort making a wrist-worn device a more attractive form factor. In this report, we detail our on-going development of a wrist-worn PPG device capable of measuring both heart rate and respiration. Our device exceeds the abilities of current commercially available wrist-worn fitness devices, which are able to measure heart rate alone, by demonstrating the ability to measure both heart rate and respiration using additional filtering and signal amplification strategies (DK Spierer, et al., 2015).

A. Feature-Packed

The device is fully-featured to include the main components to perform the physiological monitoring, as well as auxiliary features to give it the capabilities of a watch. The device contains a 9 DoF inertial measurement unit, a PCF8523 real-time clock, SD card, 0.66 in' OLED, three user input buttons, an ARM Cortex M0 Bluetooth microcontroller, external RAM, a vibration motor, a speaker, fuel gauge for monitoring battery usage, battery charging circuit, and voltage regulator. These components were designed on custom designed printed circuit boards contained within a 42 mm wide×38 mm tall×18 mm tall 3D printed enclosure.

B. Pulse and Respiration Sensor Construction

The PPG sensing circuit (FIG. 5B) is primarily composed of a photodiode, a transimpedance amplifier (TIA), and two sets of cascaded active filters. Each set of filters is specifically tuned for monitoring heart rate, which has a frequency range of 0.7 Hz to 3.5 Hz corresponding to 42 beats per minute (BPM) to 210 BPM, and respiratory rate, which has a frequency range of 0.2 Hz to 0.5 Hz corresponding to 12 breaths per minute (BrthPM) to 30 BrthPM, in healthy human adults (E L Eckberg, et al., *J. Physiol.*, 1980, 304(1), 489-502).

The TIA converts the current produced by the photodiode to a voltage. This voltage is then sent into each respective set of active filters tuned for heart and respiratory rate monitoring respectively. The outputs of our PPG sensing circuits are sensed by a microcontroller with a 10-bit analog-to-digital converter. The heart rate circuit is sampled at 11.9 Hz, while the respiration circuit is sampled at 4.0 Hz satisfying Nyquist.

C. Automatic Gain Control

The signal from the photodiode will vary with a number of physiological factors such as skin tone (J Kim, et al. *Sci. Adv.* 2016, 2(8), e1600418). As such, it is necessary to scale the gain of each amplifier stage to avoid saturating the amplifiers. To accomplish this, we employ a dynamic gain control using digitally controlled potentiometers (R3, R14, and R15 in FIG. 5B). Digital potentiometers are variable resistors that can be programmed over a serial interface such as 4-bit I²C bus/SMBus input/output expanders (sub as PCA9536 by NXP Semiconductors N.V.). By employing these digital potentiometers, we can modify the gain of each amplifier stage in software, removing the need for user intervention, and allowing the device to be portable and used in the field.

D. Comparison to Reference Standard

We compared the results from our experimental device to the BioHarness 3 from Zephyr™ Technology. The BioHarness 3 is a U.S.-FDA cleared physiological monitor available in the form of a chest strap. The device collects the electrocardiogram (ECG) signal using fabric electrodes located in the chest strap, and reports both heart and respiratory rates to the user via a convenient mobile application. The data from the BioHarness was exported using the IoTool smartphone application on a ZTE Whirl 2 Z667G Android phone. We chose to compare our device to the BioHarness due to its portability, relative low-cost, and accessible app interface. Furthermore, the device has been validated for accuracy in an earlier study (JH Kim, et al., *Int. J. Sports Med.* 2013, 34(6), 497-501).

E. Device Validation

This study was approved by the Institutional Review Board at Purdue University. As a pilot, we tested our device on two participants, Subject A and Subject B. Prior to participating in the study, both subjects gave oral and written consent. Both subjects were male in the age range of 25-34 years. Other physical characteristics of both subjects are summarized in Table 1 and each subject's skin tone is shown in FIG. 2D. Subjects were allowed to place the experimental device on either hand in accordance with the location each subject usually wears wristwatches. Subjects were instructed to place the device snugly on the wrist, to their own comfort. The device was located about 1-2 inches upwards from the wrist. Subject A placed the device on his non-dominant hand (left), while Subject B placed the device on his dominant hand (right). Each subject also wore the reference standard below the chest about even-level with the diaphragm. Measurements were taken while Subject A sat upright in a chair around a small desk. Subject B was monitored while lying flat on a couch, sleeping.

For initial benchtop validation, the discrete Fourier transform (DFT) was computed in Microsoft Excel using the "Data Analysis ToolPak" toolkit. The DFT was calculated with 128 samples using a rectangular window for both sets of measurements (heart rate and respiration). We then identified the local maxima of the resulting spectra and compared those frequencies to the respiratory and heart rates returned by the commercial device.

TABLE 1

Physical Characteristics of Participating Subjects

|  | Subject A | Subject B |
|---|---|---|
| Age Range (years) | 25-34 | 25-34 |
| Gender | Male | Male |
| Height (cm) | 175.3 | 172.7 |
| Weight (kg) | 87.1 | 106.6 |
| Skin Tone | Dark | Medium |
| Dominant Hand | Right | Right |
| Sensor Location | Left Wrist | Right Wrist |
| Testing Position | Seated Upright | Sleeping |

The sampling rates and number of samples were chosen in order to optimize frequency resolution as well as the length of sampling period. In order to collect 128 samples at 11.9 Hz for our heart rate measurements, it is necessary to sample for 11 seconds giving our heart rate determination a refresh rate of 11 seconds and a resolution of 0.09 Hz (5.4B PM). The frequencies of interest were limited to 0.7 to 3.5 Hz. The conditions for respiratory rate monitoring were determined similarly. Sampling at 4.0 Hz for 128 samples provides a refresh rate of 33 seconds and a frequency resolution of 0.03 Hz (1.8 BrthPM). The frequencies of interest were limited to 0.2 Hz to 0.5 Hz.

To properly compare the results from our device to the BioHarness, a few special considerations had to be made. The reference device returns beat-to-beat heart rate and breath-to-breath respiratory rate measurements, while the experimental device returns the rates over the respective sampling periods. As a result, we averaged the rates reported by the reference device over the same sampling periods as the experimental device.

After benchtop validation, the on-board microcontroller was programmed to compute the DFT on-chip, allowing the device to be completely portable and independent of a computer. The microcontroller was programmed according to the expression for calculating the discrete Fourier transform (DFT) using a rectangular window (J Allen, *IEEE Trans. Acoust. Speech Signal Process,* 1977, 25(3), 235-238). Care was taken to avoid performing trigonometric floating-point calculations on the microcontroller as these are computationally expensive and severely slow down our data processing. Instead, we stored the trigonometric relationships in an array of 128 values mapped as 16-bit unsigned integers between 0 and 1000. Indexing the array instead of computing the exact value of the trigonometric function increased our computing speed extensively. We then limited the calculation of the DFT to the frequencies of interests, namely 0.7 Hz to 3.5 Hz for heart rate measurements and 0.2 Hz to 0.5 Hz for respiratory rate measurements. We were able to calculate the DFT in less than 50 ms compared to 83 seconds when using the exact value of the trigonometric function.

Results and Discussion

Overall, the results from our initial pilot study showed reasonable agreement between the experimental device and the reference device. For each Subject, the error rates were within 3-4 BPM or BrthPM (accounting for rounding) as indicated in FIGS. 3A-3F. For Subject A, the experimental device reported prominent frequency content at 0.28 Hz and 1.40 Hz for heart rate, and 0.12 Hz and 0.28 Hz for respiration. The reference device reported rates of 80 BPM and 16.1 BrthPM during the sampling period, corresponding to 1.40 Hz (84 BPM) and 0.28 Hz (16.8 BrthPM) in the data collected by the experimental device. Furthermore, we observed that for Subject A, the respiratory component could be seen in the heart rate signal (FIGS. 3A and 3B at 0.28 Hz) even before further signal processing was done to amplify the respiratory signal. Data agreement was similar for Subject B. We observed frequency content at 1.21 Hz in the heart rate data and 0.12 Hz and 0.25 Hz in the respiratory data. The reference device reported an average heart rate of 73 BPM and an average respiratory rate of 15.3 BrthPM during the sampling period. This agrees with frequency content at 1.21 Hz (73 BPM) and 0.25 Hz (15 BrthPM) reported by the experimental device.

We do observe the presence of additional frequency content for each Subject and for each measurement that do not appear to be indicative of any physiological signal indicated by the reference device (0.12 Hz in respiratory rate measurements for both subjects and 0.74 Hz in the heart rate spectra for Subject A). We postulate that these additional frequency components could be due to system baseline drift and further investigation is necessary to confirm.

Figure 4A:
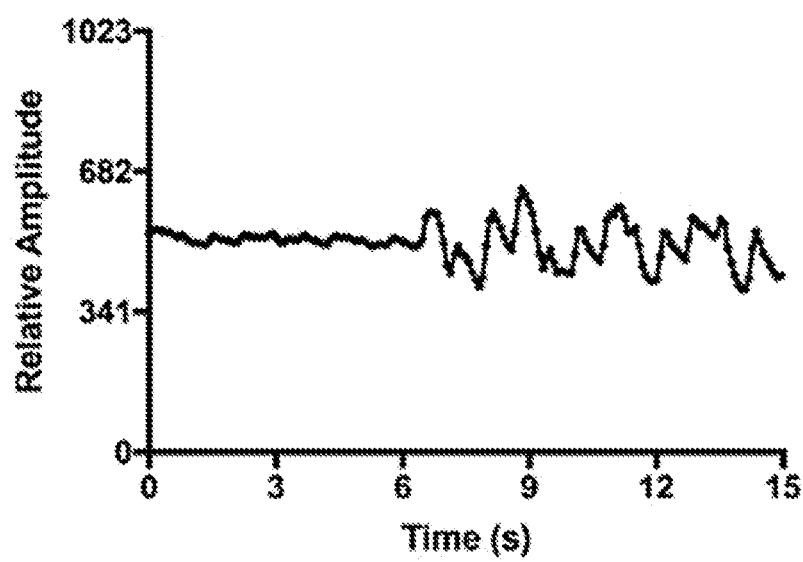
FIG. 4A shows amplitude increase in signal due to activity of auto-gain function. The microcontroller samples the dataset for the full sampling period, then adjusts the gain of the active filters to module signal amplitude.
Figure 4B:
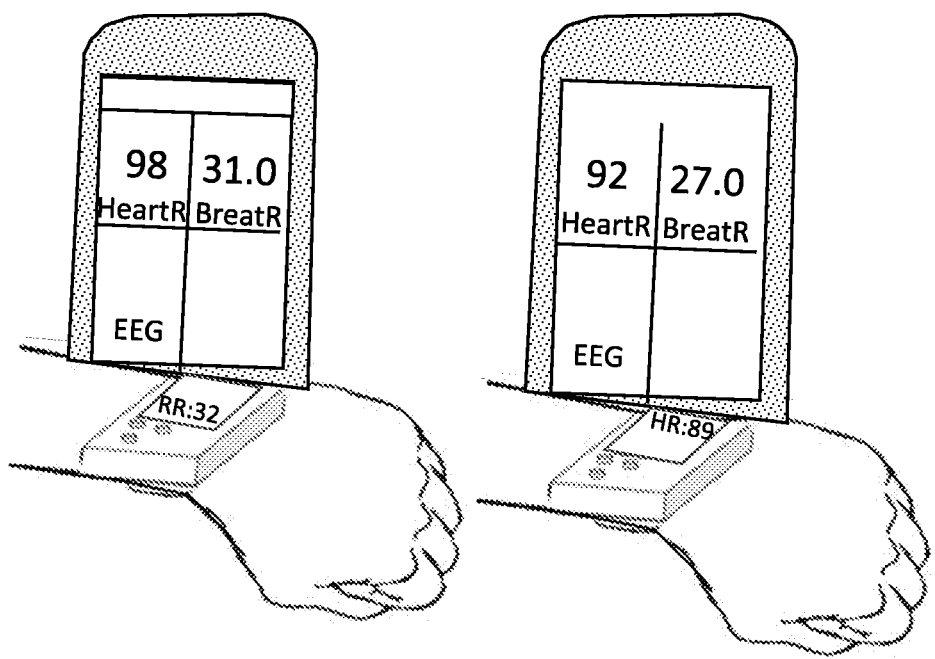
FIG. 4B shows real-time, on-board signal processing of heart and respiratory signals after a very stressful event. The refresh rate of the display is such that heart rate (HR) and respiratory rate (RR) could not be captured in a single photograph at the same time. Additionally, there is a few seconds delay between each snapshot resulting in the difference in HR and RR reported by the reference device (viewed on the smartphone), which has a faster refresh rate than the experimental device.

Furthermore, we validated our device for untethered collection of data with all processing and determination of physiological rates done on-board (FIGS. 4A and 4B.). Our respiratory rate measurements agreed within 1 BrthPM of the reference standard, while the heart rate measurements agreed within 3 BPM.

To summarize, we have presented a proof-of-concept for accurate measurements of respiration and heart rate on the wrist with a single device. Our device improves upon other wrist-worn PPG sensors, which are only capable of measuring heart rate alone, by demonstrating the ability to detect respiration in addition to heart rate. Future optimization of our algorithms will be done in order to improve the refresh rate of our measurements. We postulate this could be done by sliding our DFT computation across the sampling period. We will also increase the number of human subjects in order to validate the accuracy of our device for all-day wear.

FIG. 1 shows a prototype of a wearable device disclosed herein.

Figure 2A:
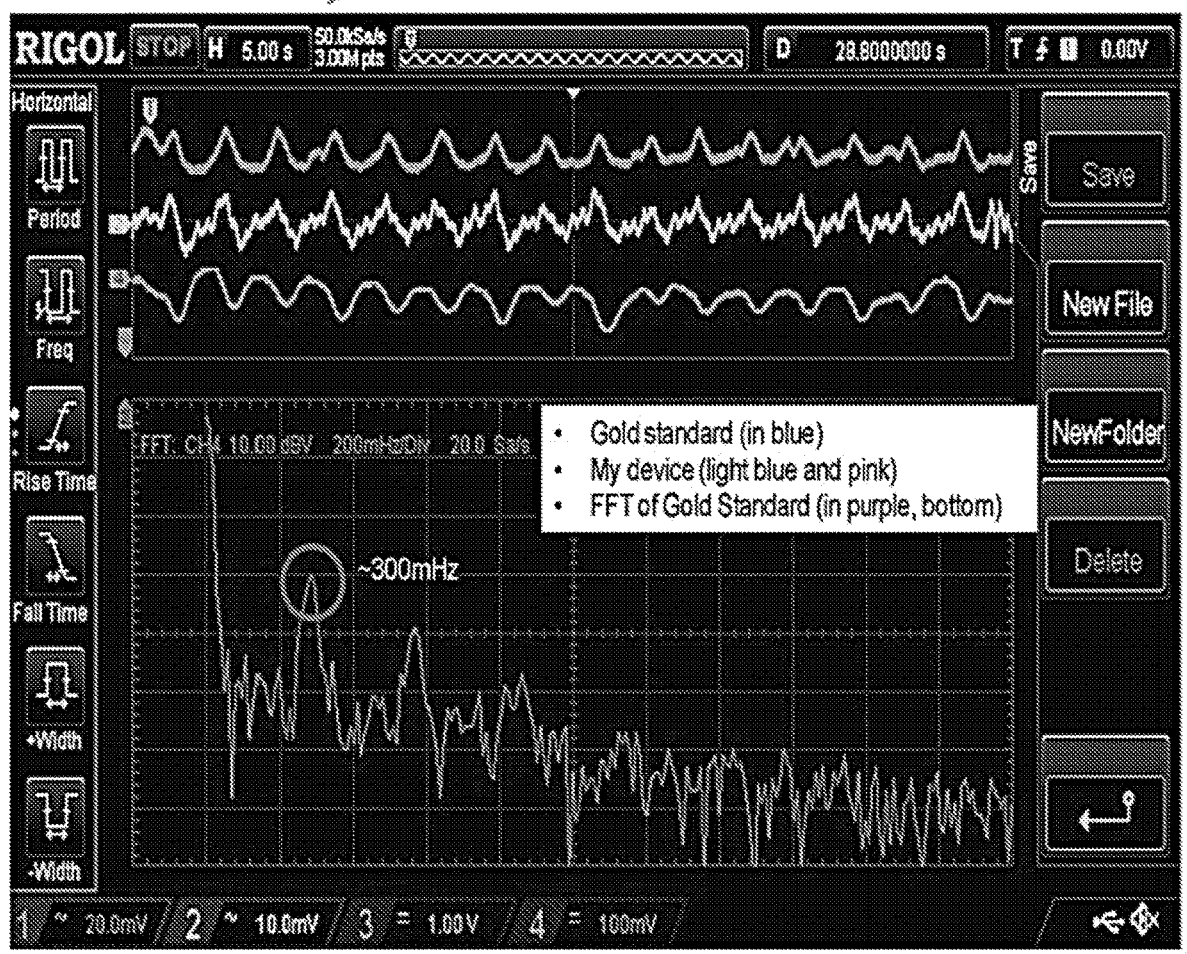
FIG. 2A depicts the waveforms (top panel) the respiration signal in real-time. The dark blue signal is the signal from the gold standard (impedance pneumograph, also known as a pneumatograph or spirograph), the light blue is the signal from our custom device, and the pink signal is also from our custom device after further amplification and filtering. The bottom graph is the fast Fourier Transform (FFT) of the gold standard. This is used to analyze the frequency components of the signal collected from the gold standard in order to calculate respiratory rate. There is a primary frequency component at around 300 mHz. Meaning the respiratory rate is about 0.3 Hz*60=18 breaths per minute.

FIG. 2A depicts the waveforms (top panel) the respiration signal in real-time. The dark blue signal is the signal from the gold standard (impedance pneumograph, also known as a pneumatograph or spirograph), the light blue is the signal from our custom device, and the pink signal is also from our custom device after further amplification and filtering. The bottom graph is the fast Fourier Transform (FFT) of the gold standard. This is used to analyze the frequency components of the signal collected from the gold standard in order to calculate respiratory rate. There is a primary frequency component at around 300 mHz. Meaning the respiratory rate is about 0.3 Hz*60=18 breaths per minute.

Figure 2B:
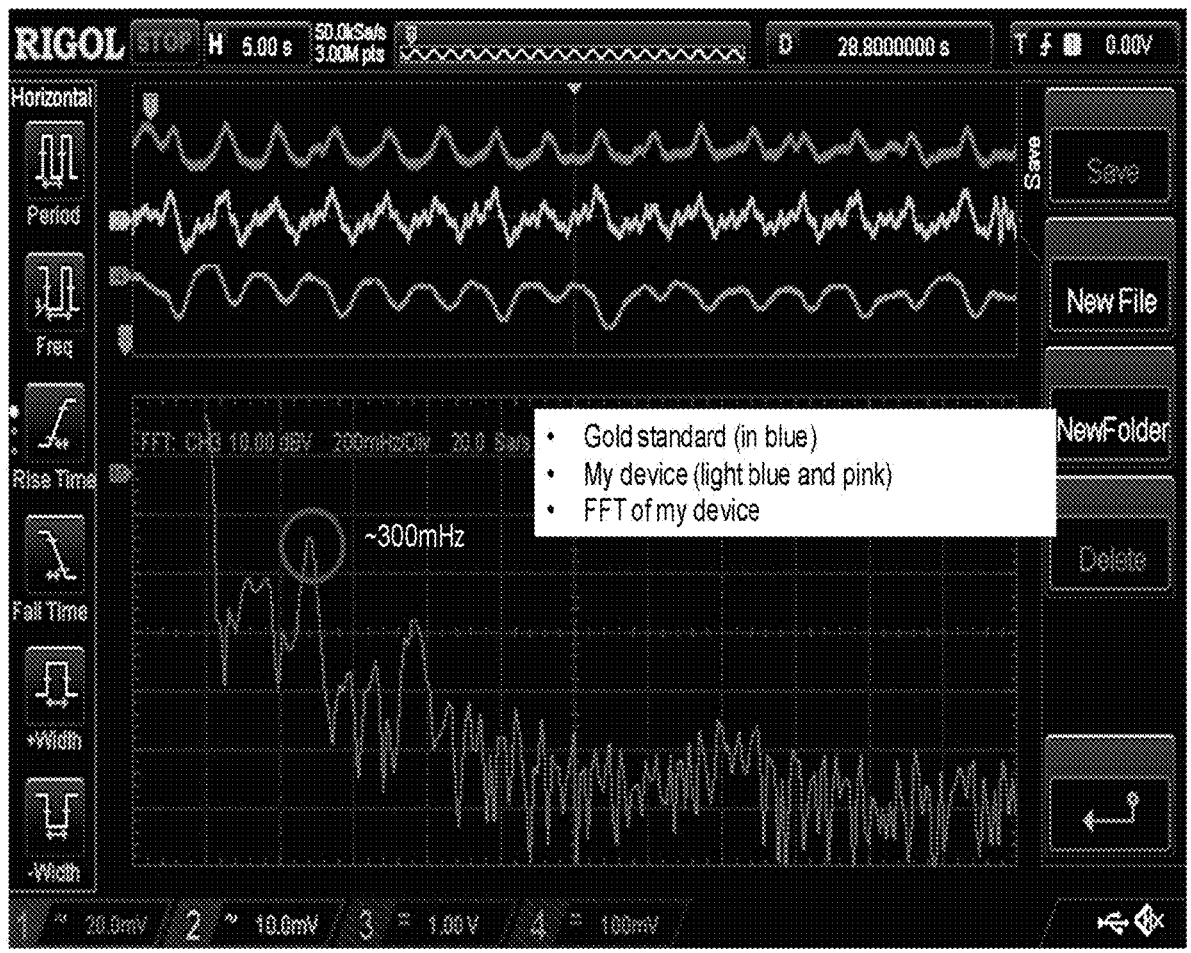
FIG. 2B shows the FFT analysis is now of our custom device. We are comparing the bottom graph of this slide to the bottom graph of slide 3. As you note, there is a primary frequency component at around 300 mHz. This primary frequency component of our custom device (bottom graph slide 4) is identical to the primary frequency component of the gold standard (bottom graph slide 3) meaning that our device was able to detect respiration as well as the gold standard.

FIG. 2B shows the FFT analysis is now of our custom device. We are comparing the bottom graph of this slide to the bottom graph of slide 3. As you note, there is a primary frequency component at around 300 mHz. This primary frequency component of our custom device (bottom graph slide 4) is identical to the primary frequency component of the gold standard (bottom graph slide 3) meaning that our device was able to detect respiration as well as the gold standard.

Figure 2C:
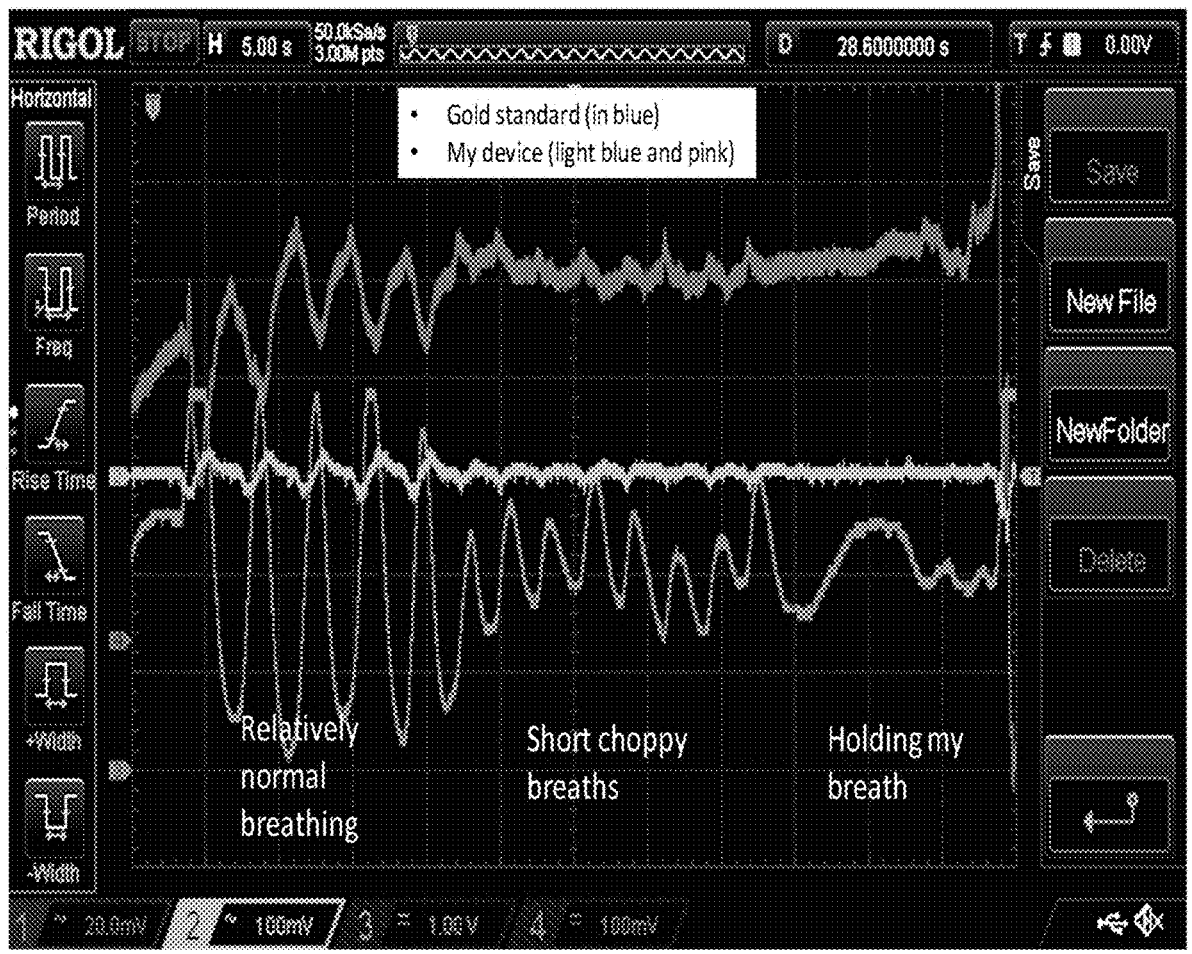
FIG. 2C shows scaled up respiratory patterns as detected by the gold standard (in dark blue), our device (in light blue), and our device again after further amplification and filtering (pink). The sinusoidal patterns measured by our device matches the gold standard for normal breathing, short choppy breaths, and holding one's breath. This slide demonstrates that our device is also able to detect breathing patterns similar to the gold standard.
Figure 2D:
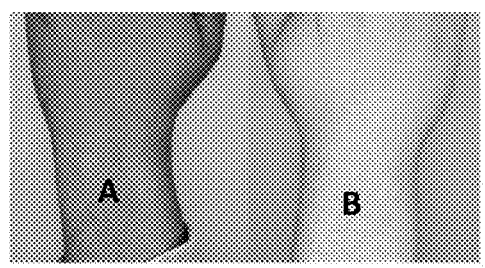
FIG. 2D shows scanned images of subjects' wrists. Images were taken with an Epson Perfection V850 Pro using the Epson Scan Windows application Version 3.9.3.2US with 24-bit color and 600 dpi resolution.

FIG. 2C shows scaled up respiratory patterns as detected by the gold standard (in dark blue), our device (in light blue), and our device again after further amplification and filtering (pink). The sinusoidal patterns measured by our device matches the gold standard for normal breathing, short choppy breaths, and holding one's breath. This slide demonstrates that our device is also able to detect breathing patterns similar to the gold standard.

Figure 3A:
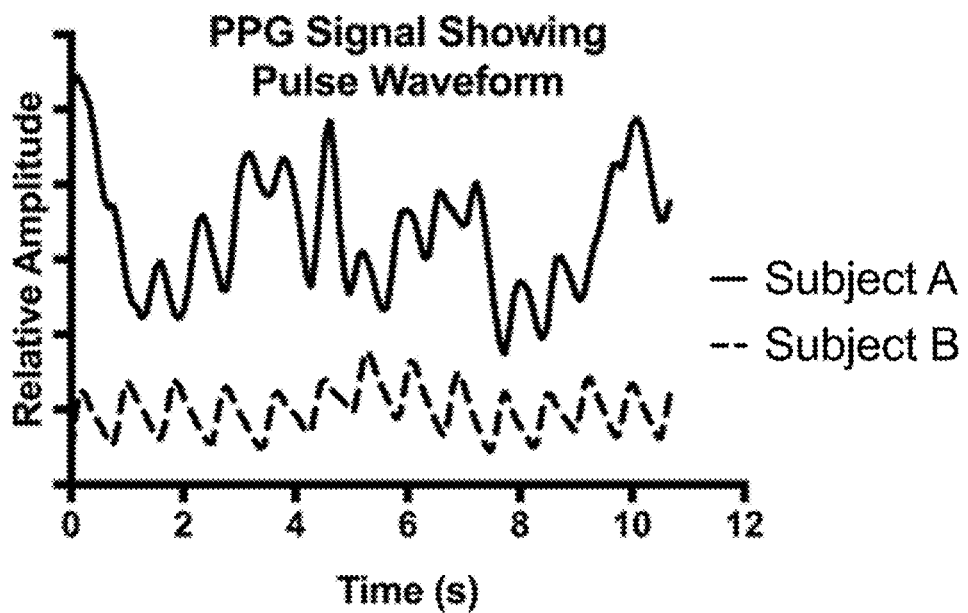
FIG. 3A shows the time domain response of the experimental device to heartbeats for Subjects A and B. We can visibly observe at least 2 frequency components in each signal, one possibly corresponding to heart rate and the other to respiration.

FIG. 3A shows the time domain response of the experimental device to heartbeats for Subjects A and B. We can visibly observe at least 2 frequency components in each signal, one possibly corresponding to heart rate and the other to respiration.

Figure 3B:
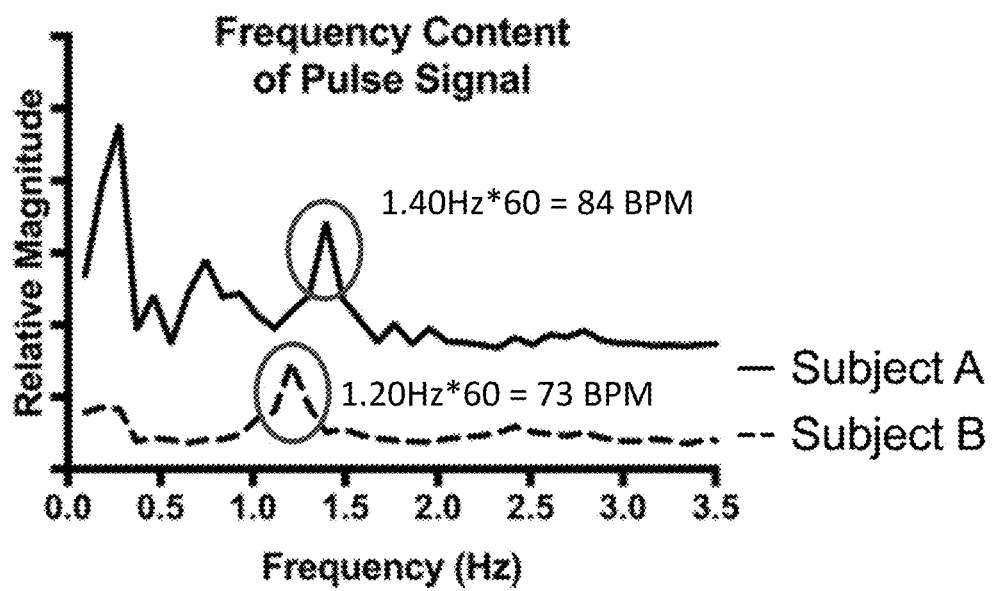
FIG. 3B shows each signal is processed in the frequency domain. Suspected frequency components indicative of heart rate are highlighted.

FIG. 3B shows each signal is processed in the frequency domain. Suspected frequency components indicative of heart rate are highlighted.

Figure 3C:
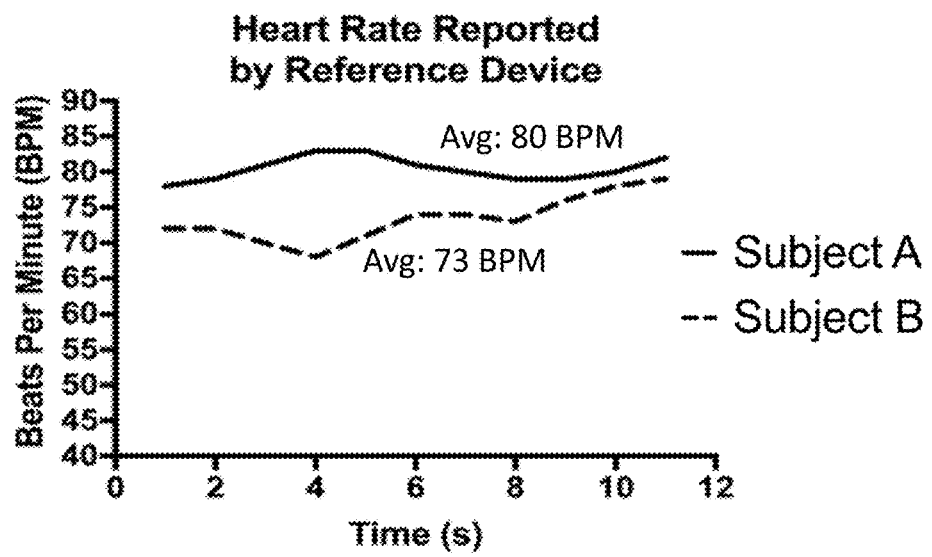
FIG. 3C shows data from the reference device indicates heart rates of 83 BPM and 73 BPM for Subjects A and B, respectively. These rates correspond to frequency components 1.40 Hz for Subject A and 1.21 Hz for Subject B.

FIG. 3C shows data from the reference device indicates heart rates of 83 BPM and 73 BPM for Subjects A and B, respectively. These rates correspond to frequency components 1.40 Hz for Subject A and 1.21 Hz for Subject B.

Figure 3D:
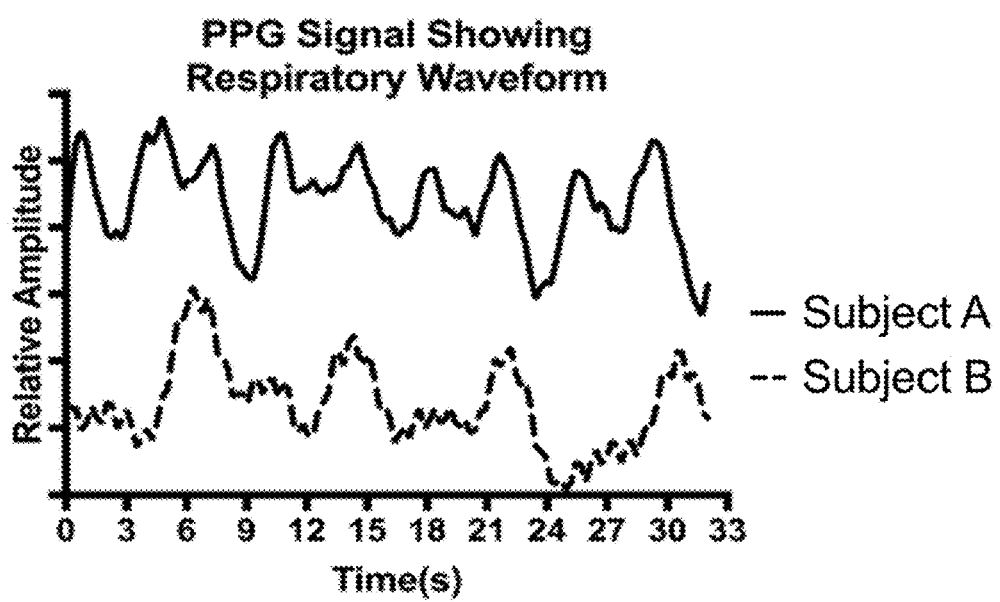
FIG. 3D shows the respiratory signal is shown. We notice slower changes in the signal on the order of several seconds compared to heart rate, which was more on the order of 1 to 1.5 seconds.

FIG. 3D shows the respiratory signal is shown. We notice slower changes in the signal on the order of several seconds compared to heart rate, which was more on the order of 1 to 1.5 seconds.

Figure 3E:
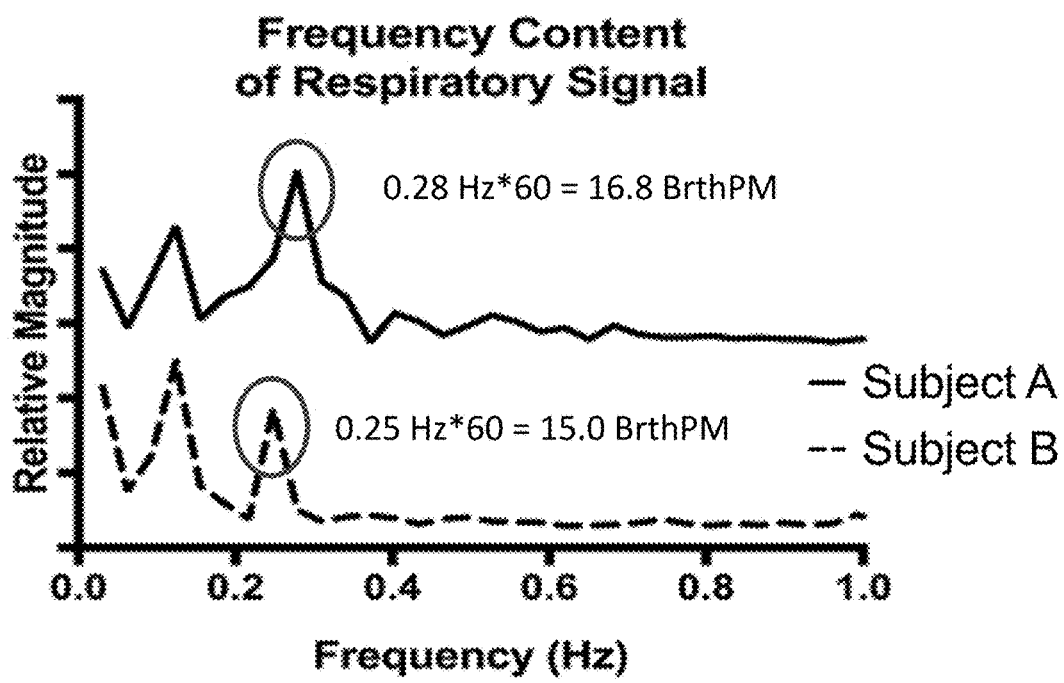
FIG. 3E shows the spectra of the respiration signals are highlighted with two dominant frequency components for each Subject (0.12 Hz and 0.28 Hz for Subject A and 0.12 Hz and 0.25 Hz for Subject B).

FIG. 3E shows the spectra of the respiration signals are highlighted with two dominant frequency components for each Subject (0.12 Hz and 0.28 Hz for Subject A and 0.12 Hz and 0.25 Hz for Subject B).

Figure 3F:
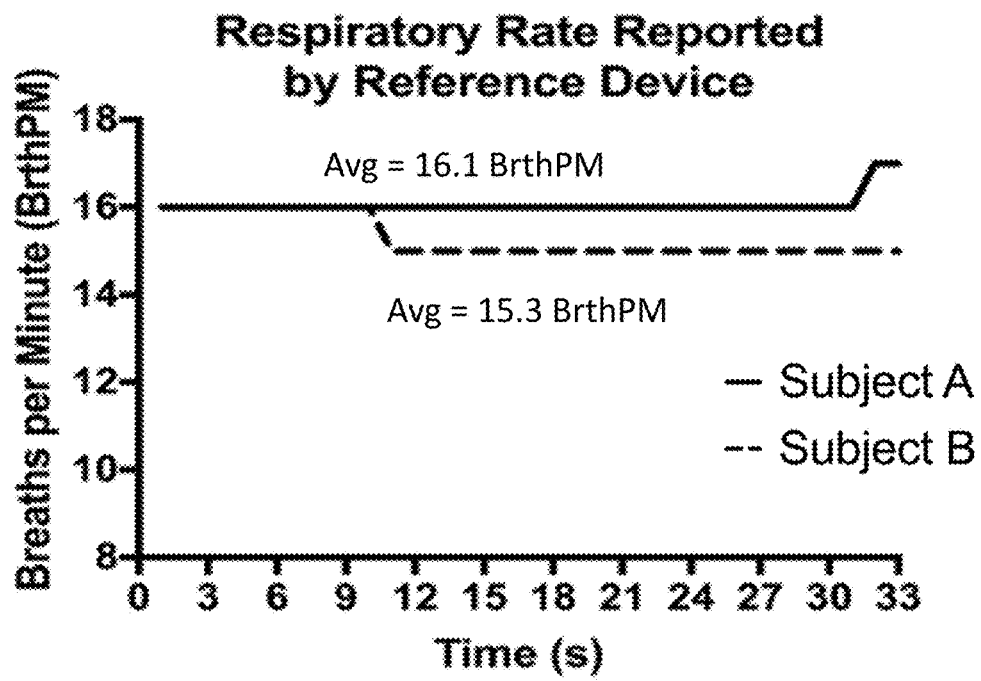
FIG. 3F shows data from the reference device indicates a respiratory rates of 16.1 breathes per minute (BrthPM) for Subject A and 15.3 Hz for Subject B. These rates correspond to peaks at 0.28 Hz (Subject A) and 0.25 Hz (Subject B) for each respective subject.

FIG. 3F shows data from the reference device indicates a respiratory rates of 16.1 BrthPM for Subject A and 15.3 Hz for Subject B. These rates correspond to peaks at 0.28 Hz (Subject A) and 0.25 Hz (Subject B) for each respective subject.

FIG. 4A shows amplitude increase in signal due to activity of auto-gain function. The microcontroller samples the dataset for the full sampling period, then adjusts the gain of the active filters to module signal amplitude.

FIG. 4B shows real-time, on-board signal processing of heart and respiratory signals after a very stressful event. The refresh rate of the display is such that heart rate (HR) and respiratory rate (RR) could not be captured in a single photograph at the same time. Additionally, there is a few seconds delay between each snapshot resulting in the difference in HR and RR reported by the reference device (viewed on the smartphone), which has a faster refresh rate than the experimental device.

Figure 5A:
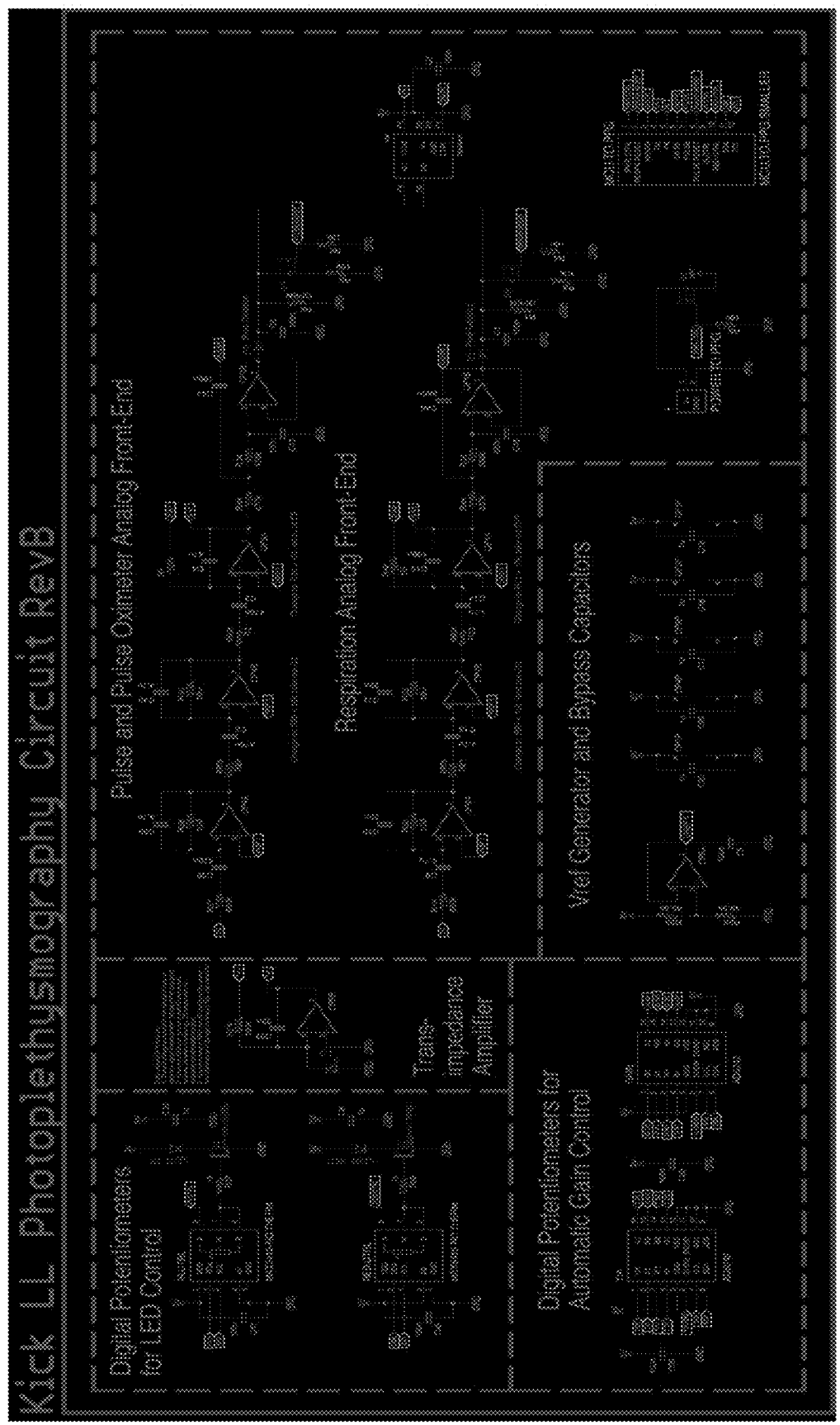
FIG. 5A shows our schematic for our biometric sensor board. In this design, we depict our amplification and filtering scheme for measuring heart rate, respiration, and pulse oximetry. We have a dual LED (red and infrared) in which we are able to automatically control the brightness of the LEDs to account for difference in skin tones.

FIG. 5A shows our schematic for our biometric sensor board. In this design, we depict our amplification and filtering scheme for measuring heart rate, respiration, and pulse oximetry. The mathematical calculation of oxygen saturation follows the methods described in the literature as demonstrated with the following formulae shown below (S Sassaroli, et al., *Phys. Med. Biol.* 2004, 49(14), N255; D. R. Tobler et al., U.S. Pat. No. 6,285,896, 4 Sep. 2001; *J M Schmitt, IEEE Transactions on Biomedical Engineering*, 1991, 38(12), 1194-1203; W. G. Zijlstra, et al., *Clinical Chemistry*, 1991, 37(9), 1633-1638). We have a dual LED (red and infrared) in which we are able to automatically control the brightness of the LEDs to account for difference in skin tones.

$$S(t) = \frac{AC(t)}{DC(t)}$$

$$R(t) = \frac{\ln(\text{rms}(S(T)_R) + 1)}{\ln(\text{rms}(S(T)_{IR}) + 1)}$$

$$(SpO)_2(t) = \frac{\varepsilon_{Hb}(\lambda_R) DPF_{R-IR} \varepsilon_{Hb}(\lambda_{IR}) R(t)}{[\varepsilon_{Hb}(\lambda_R) - \varepsilon_{HbO_2}(\lambda_R)] DPF_{R-IR} + [\varepsilon_{HbO_2}(\lambda_{IR}) - \varepsilon_{Hb}(\lambda_{IR})] R(t)}$$

The signal processing for heart rate and respiration follows four major steps: a). Discrete Fourier Transform (DFT); b) Peak Detector; c) Spectral Centroid; d) Segmentation Discrete Fourier Transform (DFT)

The DFT calculates the frequency content of our signal (R M Rangayyan, Biomedical Signal Analysis. John Wiley & Sons, 2015; J W Cooley, et al., *IEEE Transactions on Education*, 1969, 12(1), 27-34). This calculation shows how much each frequency contributes to the overall signal by calculating the "magnitude" at each frequency which is a mathematical weight representing how much a particular frequency contributes to the overall signal. We calculate the DFT for our physiological signal (heart rate or respiratory rate) as well as the signals from the accelerometer and gyroscope.

$$X(k) = \sum_{k=0}^{N-1} x(n) * \left[\cos\left(\frac{2\pi}{N}kn\right) - j*\sin\left(\frac{2\pi}{N}kn\right)\right]$$

where x(n) are the data samples and k=0 to N−1

Peak Detector.

We then employ a peak detector which finds the given frequency that has the largest contribution to the signal by comparing the magnitudes of the DFT calculation at each frequency. We also find the peak frequency in the acceleration and gyroscope data as well. The software then compares the peaks found in the physiological signal to the peaks found in the accelerometer and gyroscope. If the peaks found in the physiological signal are also found in the accelerometer and gyroscope, the frequency is considered noise. The software does this until a unique frequency in the physiological signal that is not represented in the accelerometer or gyroscope data is found.

Spectral Centroid.

Once a unique frequency is found for the physiological signal, we calculate the spectral centroid. This is a weighted average of the frequency spectrum around our unique frequency. This allows us to find small variances in our frequency analysis that could be due to small contributions by frequencies around our unique frequency (G J Sandell, *Music Percept*, 1995, 13(2), 209-246; P N Le, et al., *Speech Communication*, 2011, 53(4), 540-551; KA Wear, *IEEE Transactions on Ultrasonics, Ferroelectrics, and Frequency Control*, 2003, 50(4), 402-407).

$$\text{Centroid} = \sum_{k=0}^{N-1} \frac{f_k X(k)}{X(k)}$$

wherein, X(k) is the magnitude of the DFT for each frequency, and f, k are each individual frequency.

The Centroid value represents the most accurate frequency indicative of our physiological value, whether it be heart rate or respiration. To calculate heart rate or respiratory rate, we multiply the centroid by 60 to obtain breaths per minute or beats per minute (depending on which physiological signal we are analyzing)

Centroid*60=breaths per minute or beats per minute

Segmentation.

The software then re-analyzes the original physiological signal to into different segments. For instance, if we have N samples, the software finds N/4 or N/2 samples that have less noise in them than the entire signal itself. The software does this by observing the level of activity reported by the accelerometer and gyroscope. The software tries to find a period of time within the N samples where the level of activity reported by the accelerometer and gyroscope are low. Once the data is segmented into N/4 or N/2 samples, the software analyzes the segmented data as described above. By doing so, we can perform more accurate frequency analysis by excluding data samples that are too obscured by noise.

A computer program in a computer-readable form (CRF) is submitted concurrently with this application. The file, entitled 68015-02_computer_listing.txt, is generated on Sep. 5, 2018. The content of the computer listing is hereby incorporated by reference in its entirety. The program carries out some of the data collection, mathematic calculations, data analysis, readout and sharing.

Figure 5B:
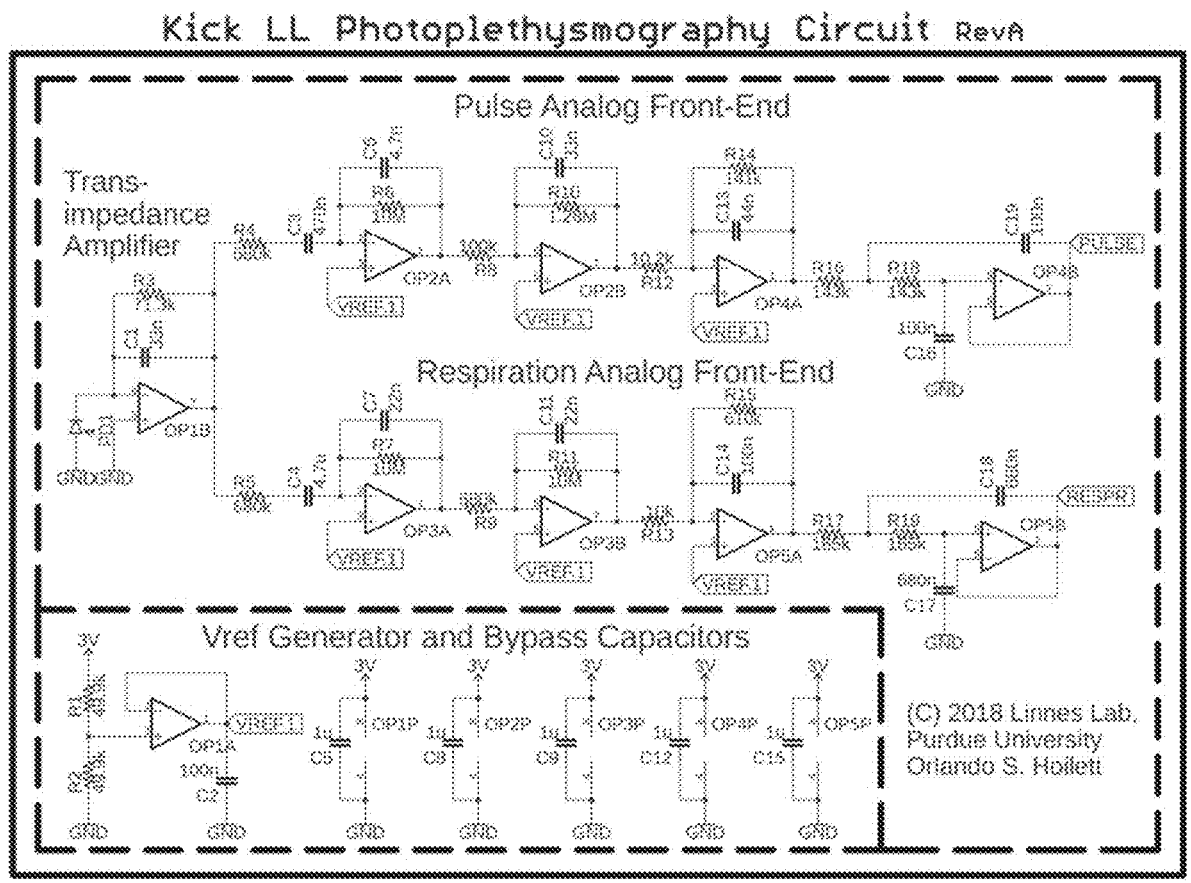
FIG. 5B shows schematic of the photoplethysmography (PPG) sensing circuit. The signal from the transimpedance amplifier is sent into two sets of cascaded active filters tuned for heart rate sensing and respiration monitoring respectively. The outputs of the amplifier stages are sensed by two channels of an on-board 10-bit analog-to-digital converter on a Bluetooth-enabled microcontroller. The signals are processed by the on-board microcontroller. R3, R14, and R15 (highlighted with a dashed box) are digitally controlled potentiometers enabling automatic gain control. Using these potentiometers, the microcontroller can modulate system gain in order to adjust for differences in the optical reflective properties of skin across difference subjects.

FIG. 5B shows schematic of the PPG sensing circuit. The signal from the transimpedance amplifier is sent into two sets of cascaded active filters tuned for heart rate sensing and respiration monitoring respectively. The outputs of the amplifier stages are sensed by two channels of an on-board 10-bit analog-to-digital converter on a Bluetooth-enabled microcontroller. The signals are processed by the on-board microcontroller. R3, R14, and R15 (highlighted with a dashed box) are digitally controlled potentiometers enabling automatic gain control. Using these potentiometers, the microcontroller can modulate system gain in order to adjust for differences in the optical reflective properties of skin across difference subjects.

Figure 6:
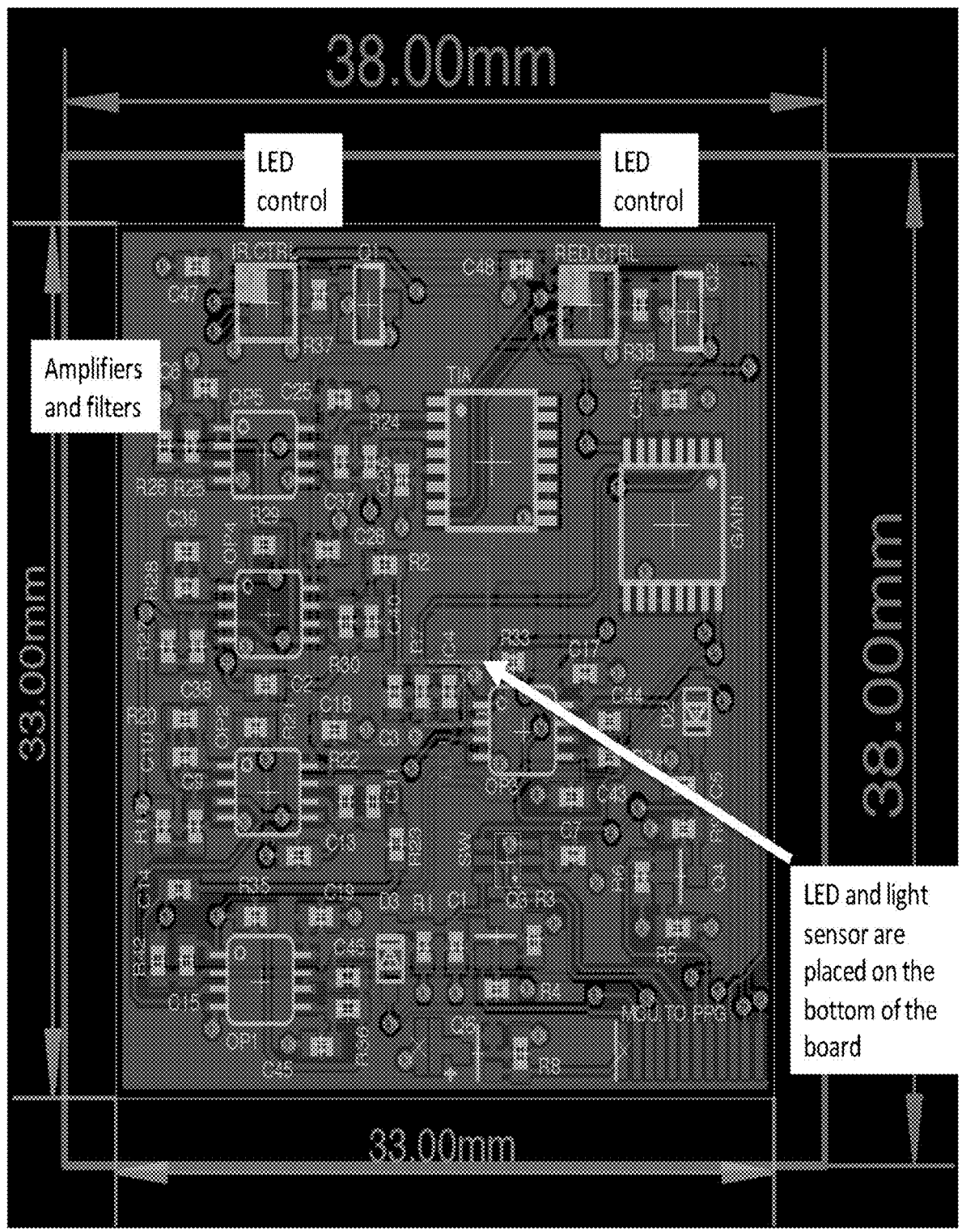
FIG. 6 depicts the circuit board design for our biometric sensor board showing how the circuit board is physically laid out in space. Along the left side are the amplifiers and filters. At the center and bottom of the board are the LEDs and light sensor. At the top is the brightness control mechanism for the LEDs.

FIG. 6 depicts the circuit board design for our biometric sensor board showing how the circuit board is physically laid out in space. Along the left side are the amplifiers and filters. At the center and bottom of the board are the LEDs and light sensor. At the top is the brightness control mechanism for the LEDs.

Figure 7:
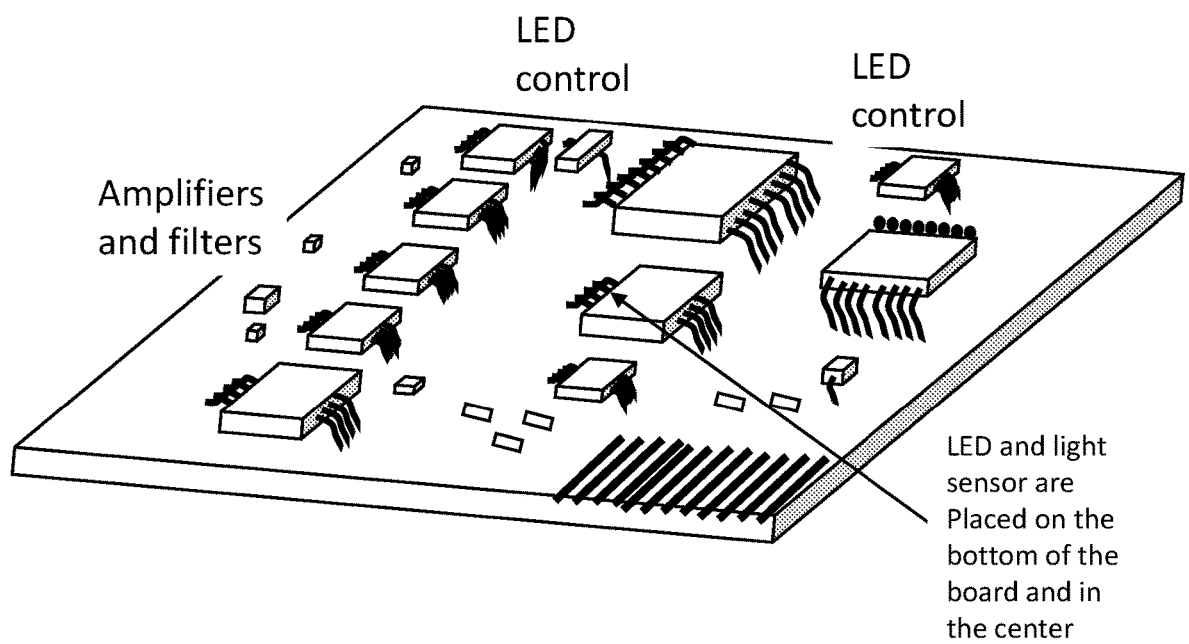
FIG. 7 shows the back side of the circuit board.

FIG. 7 shows the back side of the circuit board of FIG. 6

Figure 8:
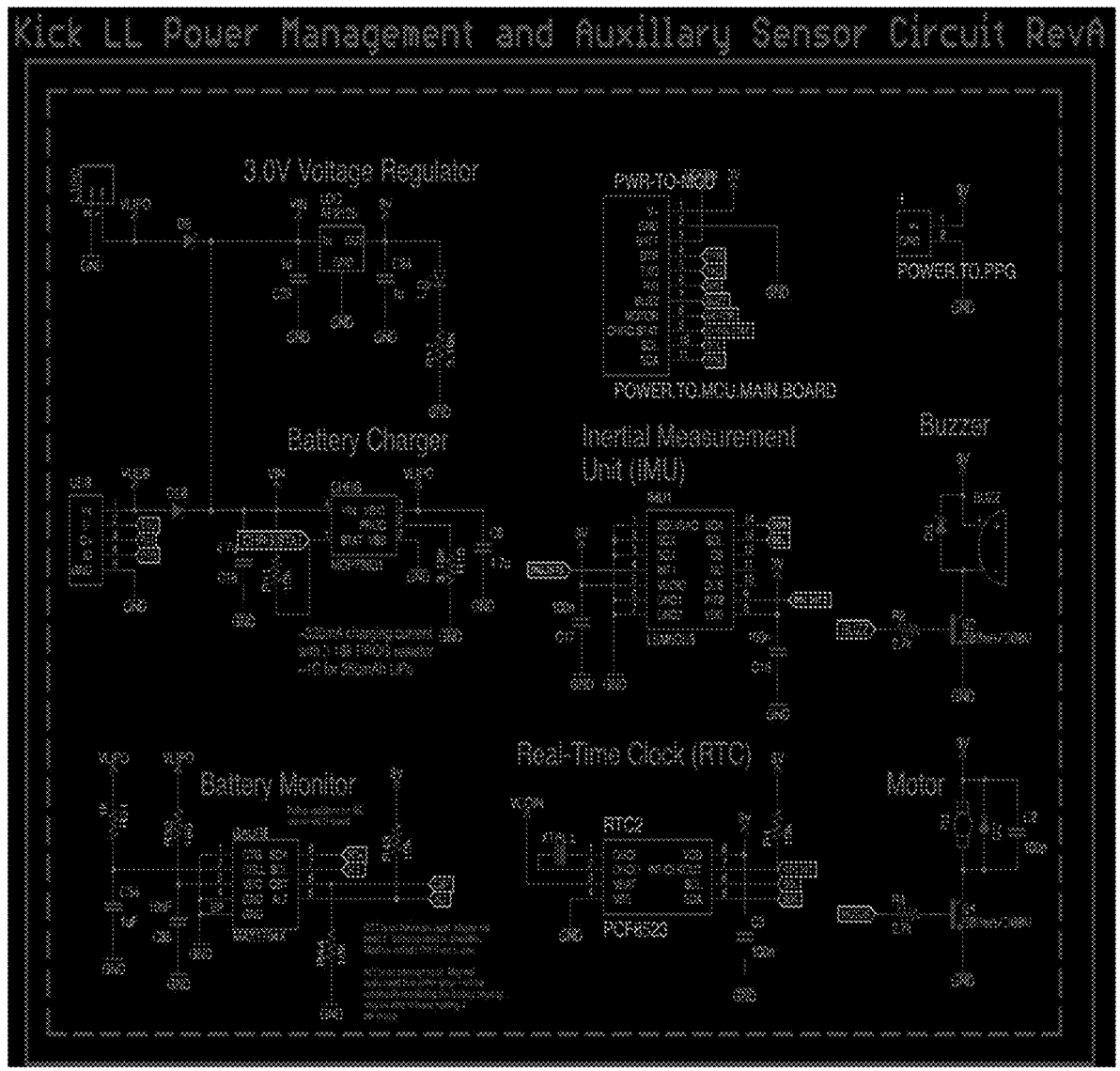
FIG. 8 shows This slide shows our auxiliary sensor board that contains battery management systems (voltage regulation, battery charging, battery status), a locomotion sensor (accelerometer and gyroscope), a real-time clock (for accurate time keeping), a motor (for user feedback), and a buzzer (also for user tactile feedback).

FIG. 8 shows the auxiliary sensor board that contains battery management systems (voltage regulation, battery charging, battery status), a locomotion sensor (accelerometer and gyroscope), a real-time clock (for accurate time keeping), a motor (for user feedback), and a buzzer (also for user tactile feedback).

Figure 9:
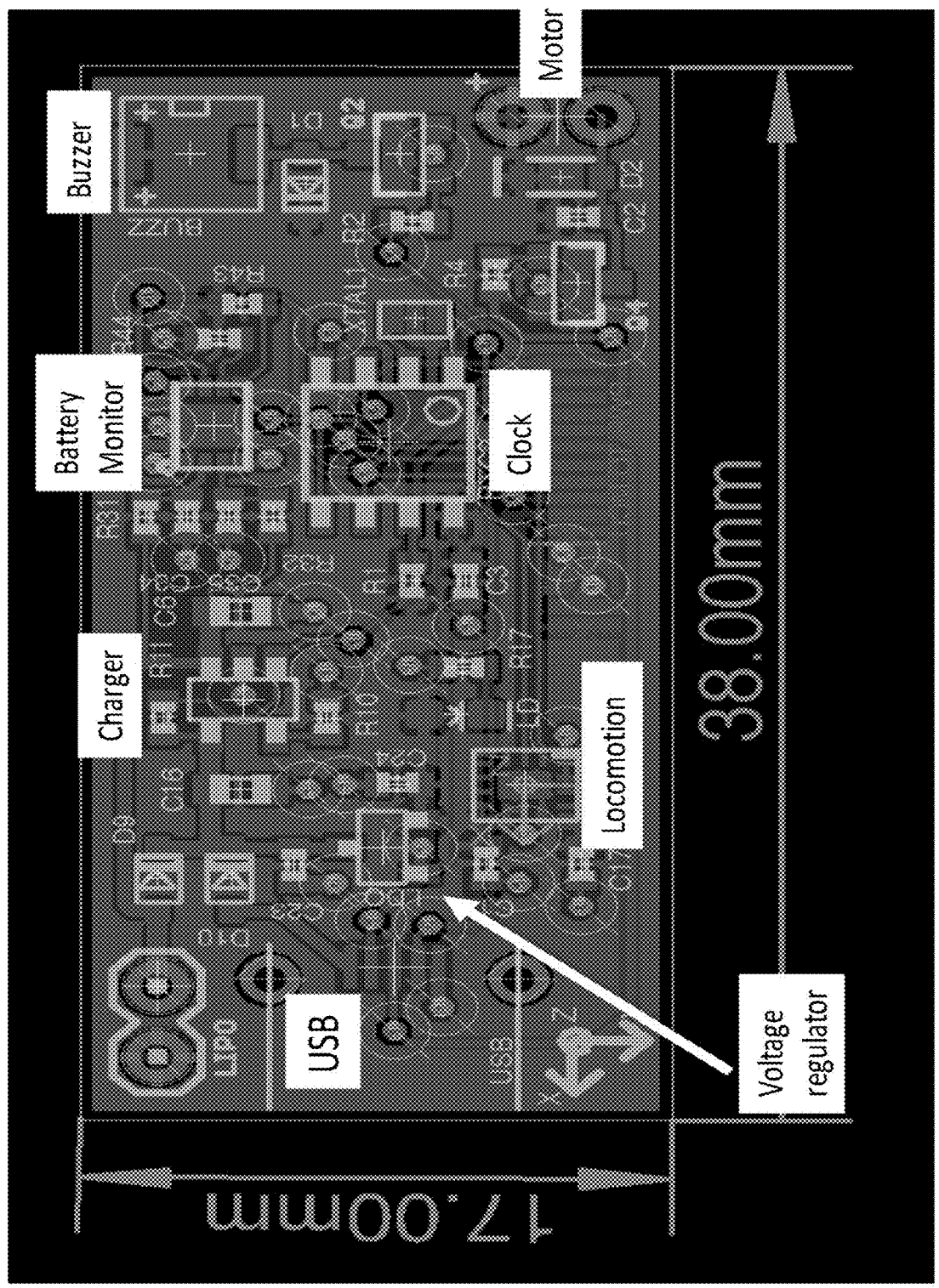
FIG. 9 shows the circuit board layout for the auxiliary sensor board and where all the components are laid out.

FIG. 9 shows the circuit board layout for the auxiliary sensor board and where all the components are laid out.

Figure 10:
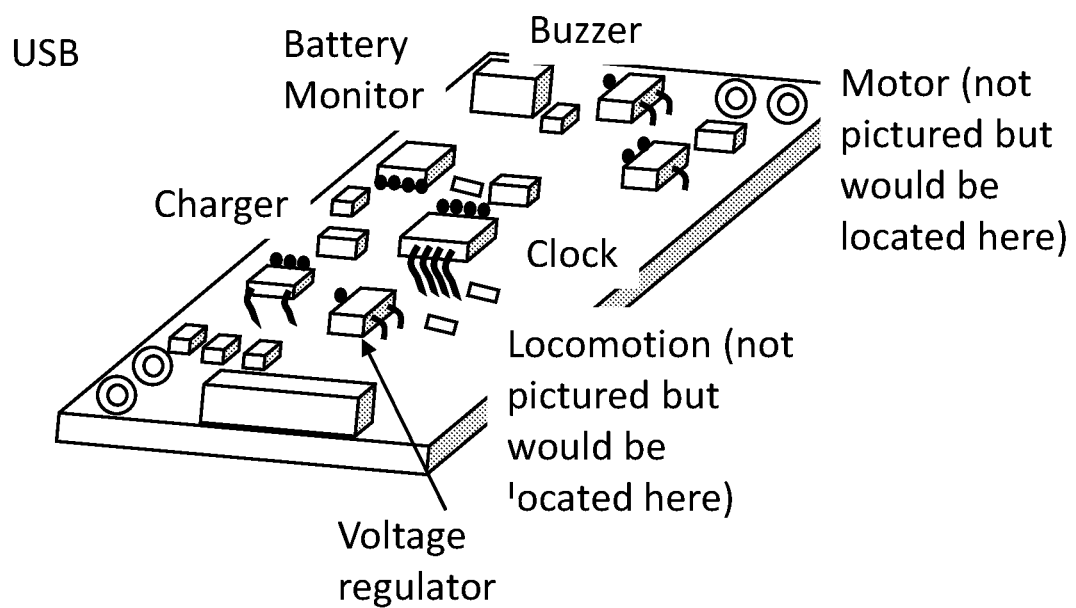
FIG. 10 shows the communications and central processing board that contains our Bluetooth capable central processing unit, an external memory chip (RAM), a screen for displaying information to the user (OLED), an SD card for long term data storage, and buttons for user input. This board handles all the data processing to measure heart rate, respiratory rate, and pulse oximetry. This board is also responsible for controlling all other boards and for sending data to the user.

FIG. 10 shows the communications and central processing board that contains our Bluetooth capable central processing unit, an external memory chip (RAM), a screen for displaying information to the user (OLED), an SD card for long term data storage, and buttons for user input. This board handles all the data processing to measure heart rate, respiratory rate, and pulse oximetry. This board is also responsible for controlling all other boards and for sending data to the user.

Figure 11A:
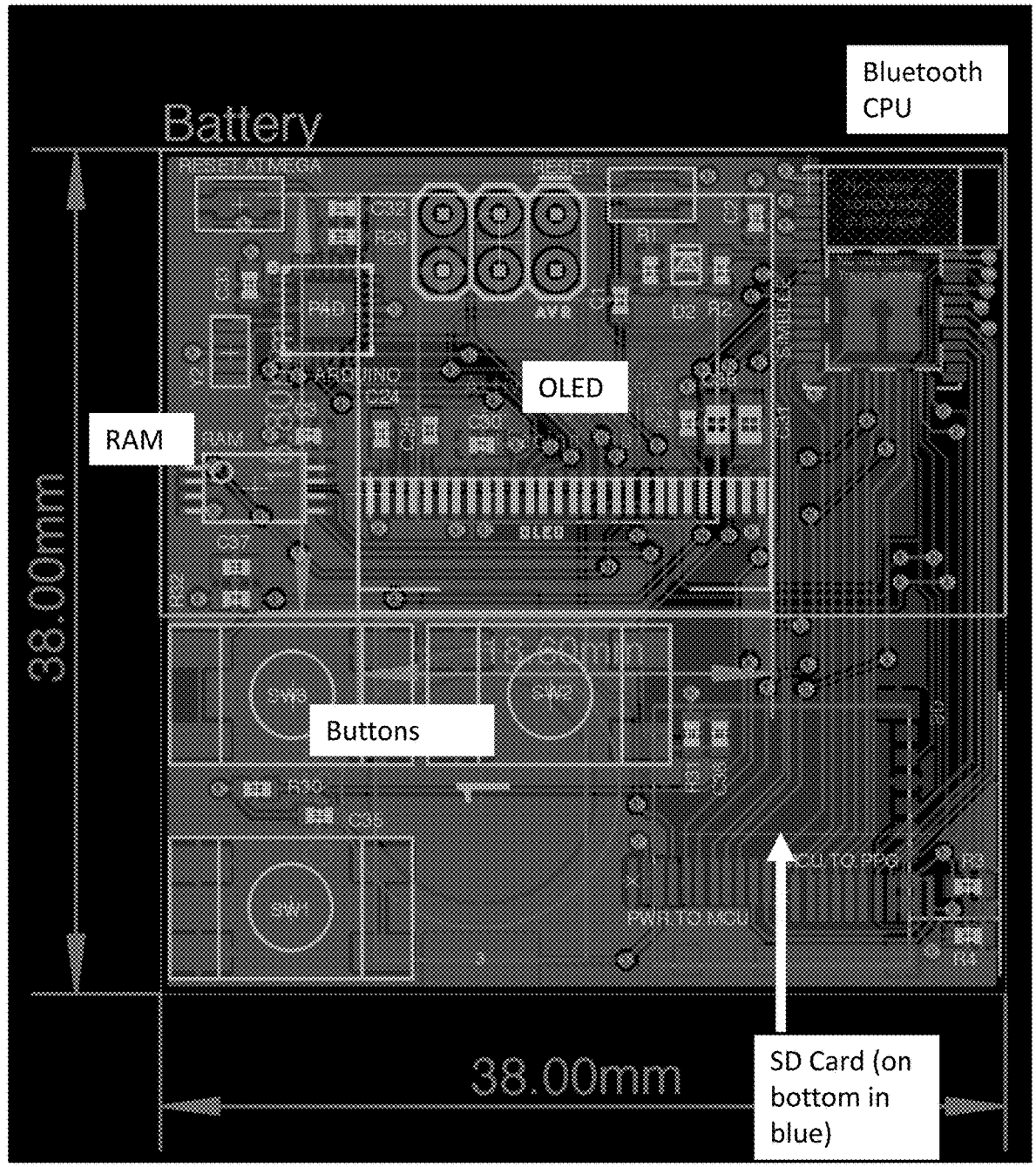
FIG. 11A depicts the circuit board layout for our communications and central processing board.
Figure 11B:
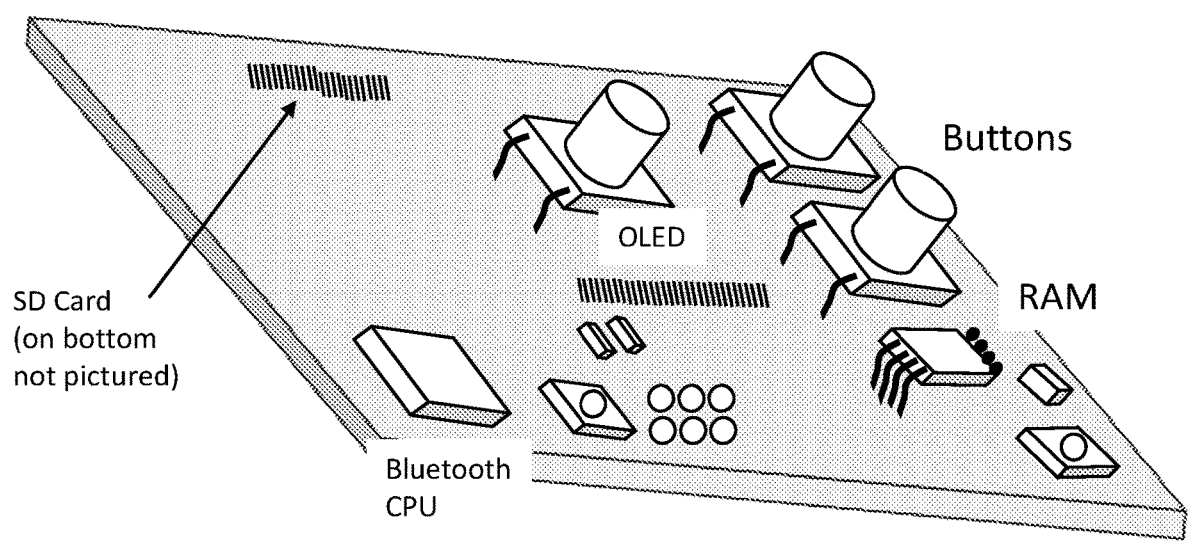
FIG. 11B shows the back side of the circuit board.

FIG. 11A depicts the circuit board layout for our communications and central processing board. FIG. 11B shows the back side of the circuit board.

It will be appreciated by persons skilled in the art that the present invention is not limited by what has been particularly shown and described herein. The details of one or more embodiments of the invention are set forth in the accompanying the description below. Other features, objects, and advantages of the invention will be apparent from the description and drawings, and from the claims.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A wearable device for measuring one or more biological parameters of a subject comprising
   a biometric sensor board having a photosensor adapted to generate a time-varying signal corresponding to reflectance of red and infrared lights off skin tissue;
   a locomotion sensor package, comprising a gyroscope and an accelerometer each generating a time-varying motion signal associated with motion with respect to three axes;
   a microcontroller having a processor processing data collected by said photosensor, wherein a dedicated memory chip is installed for storing data for real-time signal processing;
   a power supply; and
   a display adapted to provide results of the processed data, wherein to calculate a respiration rate, the processor is configured to:
      (a) sample the time-varying photosensor signal and the time-varying motion signals to thereby generate a digitized time-varying photosensor signal and digitized time-varying motion sensor signals, (b) apply a Fourier transform to the digitized time-varying photosensor signal and the digitized time-varying motion signals to thereby generate frequency domain spectra associated with magnitudes of the digitized time-varying photosensor signal and the digitized time-varying motion signals, (c) detect peaks of the magnitudes of the spectra of the digitized time-varying photosensor signal and the digitized time-varying motion signals, (d) compare the peaks of magnitudes of the frequency domain spectrum associated with the digitized time-varying photosensor signal with the peaks of magnitudes of the frequency domain spectrum associated with the digitized time-varying motion signals, (e) identify a peak present in the frequency domain spectrum associated with the digitized time-varying photosensor signal which is not present in the peaks of magnitudes of the frequency domain spectrum associated with the digitized time-varying motion signals, (f) multiply the frequency associated with the identified peak by 60 to thereby generate activity per minute.

2. The wearable device of claim 1, the processor is further configured to:

(g) compute a weighted average about the identified peak, and (h) segment the respiration rate by repeating steps a) g) with under-sampling digitized data obtained in step (a) based on one of N/2 or N/4, where N represents number of samples.

3. The wearable device of claim 2, further comprising:
active filters associated with respiration and heart rate coupled to the photosensor, and
wherein the processor is further configured to:
calculate heart rate by applying steps (a) through (h) to the associated active filter for heart rate, and
calculate respiration rate by applying steps (a) through (h) to the associated active filter for respiration rate.

4. The wearable device of claim 3, wherein filter frequency for heart rate active filter ranges from about 0.4 Hertz (Hz) to about 4 Hz; and filter frequency for respiration active filter ranges from about 0.05 Hz to about 0.5 Hz.

5. The wearable device of claim 3 to calculate oxygen saturation, the processor further configured to:
apply Beer-Lambert's law to the heart rate active filter.

6. The wearable device of claim 5, wherein said calculated heart rate, respiration, and oxygen saturation of a subject are displayed in a single display.

7. The wearable device of claim 5, wherein said calculated heart rate, respiration, and oxygen saturation of a subject are shared and/or monitored remotely.

8. The wearable device of claim 1 further comprising a real-time clock for accurate time keeping and a means for battery level monitoring.

9. The wearable device of claim 1 further comprising input and output capabilities for charging, programming, and data transfer and sharing.

10. The wearable device of claim 1 further comprising an SD card and RAM for long term and short term data storage, respectively.

* * * * *